United States Patent [19]

Desmonceau et al.

[11] Patent Number: 5,028,653

[45] Date of Patent: Jul. 2, 1991

[54] NON-AGGLOMERATING ELASTOMERIC ORGANOPOLYSILOXANE PARTICULATES PRODUCED BY POLYADDITION CROSSLINKING

[75] Inventors: Daniel Desmonceau, Rillieux La Pape; Rafael Jorda, Sainte Foy Les Lyon, both of France

[73] Assignee: Rhone-Poulenc Chimie, Courbevoie, France

[21] Appl. No.: 467,270

[22] Filed: Jan. 19, 1990

[30] Foreign Application Priority Data

Jan. 19, 1989 [FR] France ................................ 89 00862

[51] Int. Cl.$^5$ ............................................. C08K 3/36
[52] U.S. Cl. .................................. 524/462; 523/209; 524/493; 524/588; 524/745
[58] Field of Search ............... 524/588, 745, 462, 493; 523/209; 525/476, 478

[56] References Cited

U.S. PATENT DOCUMENTS

| | | | |
|---|---|---|---|
| 4,248,751 | 2/1981 | Willing | 528/32 |
| 4,370,160 | 1/1983 | Ziemelis | 524/862 |
| 4,594,134 | 6/1986 | Hanada et al. | 528/24 |
| 4,761,454 | 8/1988 | Oba et al. | 524/588 |

FOREIGN PATENT DOCUMENTS

| | | |
|---|---|---|
| 217257 | 4/1987 | European Pat. Off. . |
| 0242219 | 10/1987 | European Pat. Off. . |
| 252510 | 1/1988 | European Pat. Off. . |
| 267003 | 5/1988 | European Pat. Off. . |
| 0277740 | 10/1988 | European Pat. Off. . |
| 0304946 | 1/1989 | European Pat. Off. . |
| 2836145 | 3/1979 | Fed. Rep. of Germany . |

*Primary Examiner*—Veronica P. Hoke
*Attorney, Agent, or Firm*—Burns, Doane, Swecker and Mathis

[57] ABSTRACT

Non-agglomerating elastomeric organopolysiloxane particulates having a mean particle size ranging from 50 μm to 3 mm, uniformly coated with silica powder on the face surfaces thereof and well adapted as a soft filler material for natural or synthetic polymers or as a controlled release dosage form, are produced by (a) forming an oil-in-water emulsion of silicone oils, silica powder, a platinum curing catalyst and, optionally, an active principle such as a medicament or an agrochemical, and then (b) breaking and polyaddition crosslinking such emulsion into the desired particles by heating it to a temperature ranging from 40° to 100° C.

21 Claims, No Drawings

NON-AGGLOMERATING ELASTOMERIC ORGANOPOLYSILOXANE PARTICULATES PRODUCED BY POLYADDITION CROSSLINKING

CROSS-REFERENCE TO COMPANION APPLICATIONS

Copending applications Ser. No. 467,372 and Ser. No. 467,417, both filed concurrently herewith and assigned to the assignee hereof.

BACKGROUND OF THE INVENTION

1. Field of the Invention

The present invention relates to the preparation of non-stick (non-agglomerating) particles based on a crosslinked organopolysiloxane composition, especially elastomer particulates produced by polyaddition crosslinking, which particulates may contain an active principle encapsulated by and/or dispersed within the elastomer.

2. Description of the Prior Art

There is an increasing demand in this art for silicone elastomer particles with a view to their use in two principal types of applications:

(a) incorporation of these particles as filler material into a polymer matrix, in particular into a crosslinkable organopolysiloxane composition to produce an elastomer, with a view especially to an enhancement of flexibility, and (b) conditioning (encapsulation or dispersion) of an active principle by these particles, with a view to the protection and ultimately controlled release thereof.

Among the numerous patents describing processes for the preparation of silicone elastomer particles or microparticles crosslinked by polyaddition and/or polycondensation reactions, the following are particularly representative:

EP-A-252,510, which describes a process comprising mixing the various constituents of a liquid silicone elastomer, which may contain a siliceous filler, at a temperature ranging from $-60°$ C. to $+5°$ C. and then atomizing the mixture in air heated to a temperature of from $+80°$ C. to $200°$ C., in order to produce particles of substantially spherical shape and of a particle size ranging from a few tens of millimicrometers to several hundreds of micrometers;

U.S. Pat. No. 4,248,751, describing a process for the preparation of a silicone latex of polyaddition silicone elastomer particles dispersed in an aqueous phase, which entails polymerizing, in aqueous emulsion, a mixture of vinylated silicone oils, hydrogen-containing silicone oils and a surfactant, and then crosslinking such oils by heating after addition of a platinum catalyst (it is possible to add a colloidal silica to the latex in order to improve the properties of the film-forming elastomer covering obtained after coating of the latex onto a support and evaporation of the water, but this patent neither describes nor suggests the preparation of silicone elastomer particles having a particle size greater than 50 $\mu$m from the latex emulsion);

EP-A-217,257, describing a process for the preparation of silicone particles of a particle size of from 0.01 to 10 mm, including emulsion-polymerizing a diorganocyclopolysiloxane bearing vinyl and mercaptoalkyl groups in the presence of an alkylarylsulfonic acid, breaking the emulsion by adding magnesium sulfate thereto and by heating, introducing a vinyl monomer and effecting a graft polymerization in the presence of a free radical initiator;

U.S. Pat. No. 4,594,134 which describes the preparation of microparticles or spherical particles, of a particle size ranging from 2 to 300 $\mu$m, of silicone polyaddition elastomer, produced by atomization of a platinum-catalyzed composition, including an inhibitor of the platinum, in a dryer at about 230° C. The crosslinking can be effected without platinum and under UV irradiation, but with a photosensitizer. Prior to crosslinking, the composition can be dispersed in a liquid medium such as an organic solvent or water;

Japanese Kokai 87/257,939, describing the preparation of a silicone powder by drying and atomization of an aqueous emulsion of a polyaddition silicone composition;

Ep-A-267,003, which describes the preparation of microspheres of silicone elastomer by dispersing, in water in the presence of a surfactant, an organopolysiloxane composition which is crosslinkable by addition reactions of the MICHAEL type, and crosslinking of the composition;

U.S. Pat. No. 4,370,160, describing a process similar to EP-A-267,003, except that the organopolysiloxane composition is crosslinked under UV irradiation in the presence of a photosensitizer.

SUMMARY OF THE INVENTION

Accordingly, a major object of the present invention is the provision of improved particulates based on a crosslinked elastomeric organopolysiloxane composition, which improved particulates are directly produced and are storable and easy to handle, and, thus, do not agglomerate.

Another object of the present invention is the provision of a process for the preparation of particles directly from commercially available polycondensation organopolysiloxane compositions.

Still another object of the present invention is the provision of a process for the preparation of particles of the above type, such particles being adapted for easy incorporation, homogeneously, as filler material in a matrix of synthetic or natural polymer, in particular in a silicone elastomer.

Yet another object of this invention is the provision of a process for the preparation of polycondensation silicone elastomer particles, which permits either direct encapsulation, or homogeneous dispersion within the elastomer, of any active principle for purposes of the protection and ultimate controlled release thereof.

Briefly, the present invention features the preparation of non-stick particles having a mean particle size ranging from 50 $\mu$m to 3 mm, based on a crosslinkable organopolysiloxane composition which provides an elastomer by polycondensation reactions, which entails:

(a) preparing an emulsion from:

(A) 100 parts by weight of a polydiorganosiloxane bearing at least two Si-vinyl groups per molecule and having vinyldiorganosiloxy endgroups;

(B) an organohydrogenopolysiloxane bearing at least three SiH groups per molecule in such an amount that the SiH/SiVi molar ratio ranges from 0.6 to 8, preferably from 0.8 to 4;

(C) a catalytically effective amount of a platinum catalyst;

(D) an effective amount of a surfactant of the oil-in-water type;

(E) 3 to 100 parts by weight, preferably 5 to 30 parts, of a pyrogenic or precipitated silica powder;

(F) water; and, if appropriate;

(G) an active principle; and (b) then forming said particles by heating such emulsion to a temperature ranging from 40° to 100° C.

DETAILED DESCRIPTION OF THE PREFERRED EMBODIMENTS OF THE INVENTION

More particularly according to the present invention, in a preferred embodiment thereof, the emulsion contains a volatile organic solvent, the boiling point of which is below 100° C., such as, for example, chloroform ($CHCl_3$).

The use of a volatile organic solvent presents several advantages:

(i) it permits easy emulsification, in water, of the organopolysiloxane composition, even if this latter is a commercial composition in the form of two packages (or components), with or without fillers already incorporated into one of the two packages; and (ii) during stage (b), the organic solvent evaporates and the aqueous emulsion is then broken, which facilitates formation of the particles.

The active principle (G) can be introduced in a variety of ways into the emulsion:

(1) if the active principle is soluble in the volatile organic solvent, it can be introduced in solution in such solvent;

(2) if the active principle is soluble in water, it is desirable that the water of emulsion be saturated with the active principle (in this manner, the major part of the active principle is homogeneously dispersed within the particles); or (3) if the active principle (G) is insoluble in water and in the volatile organic solvent, it is introduced in the form of particles dispersed in the organopolysiloxane composition, preferably in the starting silicone oils (A), these microparticles being encapsulated during the stage (b).

After stage (b) has been completed, the particles are filtered off, if desired washed with an alcohol, in particular methanol, then dried in order to eliminate the residual water and to complete, if necessary, the crosslinking of the organopolysiloxane composition.

The dry particles are then screened according to predetermined particle sizes in order to eliminate any excess of silica.

The present invention thus enables the production of particles having a mean particle size ranging from 50 $\mu m$ to 3 mm, more preferably ranging from 100 $\mu m$ to 1 mm.

The diorganopolysiloxane (A), having a viscosity of 100 to 300,000 mPa.s at 25° C., preferably 600 to 200,000 mPa.s at 25° C., comprises a linear polymer including diorganosiloxy recurring structural units blocked at the polymer chain ends by a vinyl diorganosiloxy unit. The organic radicals bonded to the silicon atoms of the polymer are preferably selected from among methyl, ethyl, n-propyl, phenyl and 3,3,3-trifluoropropyl radicals. Preferably, at least 90 mol % of these radicals are methyl radicals, and at most 10 mol % are phenyl radicals.

Exemplary of such diorganosiloxy recurring units are those of the formulae: $(CH_3)_2SiO$, $CH_3(C_6H_5)SiO$, $(C_6H_5)_2SiO$, $CH_3(n\text{-}C_3H_7)SiO$ and $CH_3(C_6H_5)SiO$.

Preferably, a dimethylpolysiloxane oil blocked at each end of its polymer chain by a dimethylvinylsiloxy unit or methylphenylvinylsiloxy unit and having a viscosity from 300 to 150,000 mPa.s at 25° C. is used.

The vinylated oil (A) described above is commercially available from the various manufacturers of silicones.

In order to improve the mechanical properties of the elastomer, it is recommended to incorporate as the organopolysiloxane (A) an organopolysiloxane resin which is solid at ambient temperature and contains M and Q units of the formulae $R_3SiO_{0.5}$ and $SiO_2$, respectively, in which R is selected from among methyl, ethyl, n-propyl, phenyl and vinyl radicals, and in which resin, on the one hand, the M/Q molar ratio ranges from 0.5 to 1 and, on the other, 1.5 to 10 moles of silicon atoms bear a vinyl radical directly bonded to a silicon atom.

In addition, this resin can also contain a unit D of the formula $R_2SiO$, R being as defined above, in such manner that 1 to 10 moles of unit D remain, relative to the total number of MDQ units present in the resin.

The organohydrogenosiloxane (B) can be a linear, cyclic or branched polymer or mixture thereof, containing siloxane recurring units of the formulae $R'SiO_{1.5}$, $R'_2SiO$, $R'_3SiO_{0.5}$, $R'_2HSiO_{0.5}$, $SiO_2$, $R'HSiO$ and $HSiO_{1.5}$, in which the radical R' has the same definition as that given above for the organic radicals of the diorganopolysiloxane (A).

These siloxanes are described, for example, in U.S. Pat. Nos. 2,486,162, 3,284,406 and 3,436,366.

In a preferred embodiment of the invention, and in order to produce silicone elastomer particles having an enhanced hydrophilic and/or organophilic character, the diorganopolysiloxane (A) is wholly or partially replaced by a diorganopolysiloxane ($A_1$) which additionally contains, with respect to the diorganopolysiloxane (A), at least one organic epoxy-functional radical having from 4 to 20 carbon atoms.

The organohydrogenopolysiloxane (B) can also be wholly or partially replaced by an organohydrogenopolysiloxane ($B_1$) which additionally contains, with respect to the diorganopolysiloxane (B), at least one organic epoxy-functional radical having from 4 to 20 carbon atoms.

It is also possible to wholly or partially replace the polymers (A) and (B) by the polymers ($A_1$) and ($B_1$).

The diorganopolysiloxanes ($A_1$) are preferably selected from among those of the formula:

$$R_1-\underset{R}{\underset{|}{\overset{R}{\overset{|}{Si}}}}-O-\left[\underset{R}{\underset{|}{\overset{R}{\overset{|}{Si}}}}-O\right]_r\left[\underset{\underset{CH_2}{\overset{||}{CH}}}{\overset{R}{\overset{|}{Si}}}-O\right]_s\left[\underset{A}{\underset{|}{\overset{R}{\overset{|}{Si}}}}-O\right]_t\underset{R}{\underset{|}{\overset{R}{\overset{|}{Si}}}}-R_1 \quad (1)$$

in which the radicals R are monovalent hydrocarbon radicals selected from among $C_1$–$C_{20}$-alkyl radicals phenyl radicals, methyl radicals and 3,3,3-trifluoropropyl radicals; the radicals $R_1$, which can be identical or different, are selected from among a radical R, a radical A, a vinyl radical and a hydroxyl radical; the radical A is an organic epoxy-functional radical having from 4 to 20 carbon atoms, r is an integer ranging from 1 to 500; s is an integer ranging from 0 to 200; and t is an integer ranging from 0 to 100, with the proviso that, if s=0, the two radicals $R_1$ are each a vinyl radical and t is at least equal to 1, and, if t=0, at least one of the radicals $R_1$ is a radical A and s is at least equal to 2.

In the above formula (1), the preferred siloxanes are those in which at least 80% and up to 100% of the number of radicals R are methyl radicals.

The organic epoxy-functional radical has from 4 to 20 and preferably from 5 to 12 carbon atoms.

The following are exemplary of the radicals A:

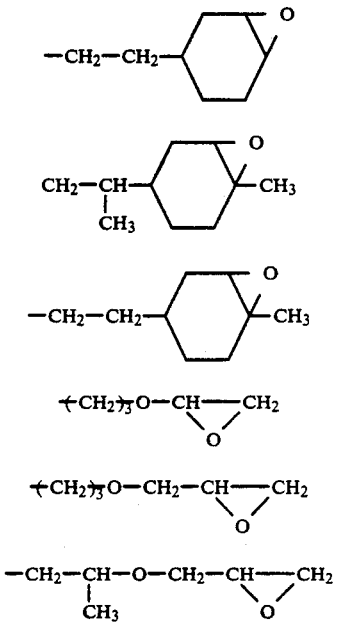

In the formula (1), s and t are preferably at least equal to 1, and r ranges from 5 to 300, inclusive.

More preferably, s ranges from 2 to 20, inclusive, t ranges from 1 to 30, inclusive, and r ranges from 5 to 100, inclusive.

The polydiorganosiloxanes ($A_1$) can be prepared in the following manner:

(i) in a first stage, polymerizing at least one cyclic or linear polydiorganosiloxane oligomer bearing, per molecule, at least one vinyl radical directly bonded to the silicon atom, in the presence of a catalytically effective amount of a basic catalyst; and (ii) in a second stage, in the time interval between the start and the completion of the polymerization of the first stage, adding to the polymerization recipe at least one cyclic or linear polydiorganosiloxane oligomer bearing, per molecule, at least one organic epoxy-functional radical having 4 to 20 carbon atoms.

Such process is described, in detail, in published French Patent Application 88/04,138, filed Mar. 24, 1988 and assigned to the assignee hereof.

The linear or cyclic oligomers bearing a vinyl group are known compounds. They are described, in particular, in the Noll text, *Chemistry and Technology of Silicones*, Academic Press, published 1968 in English, and also in numerous patents (e.g., U.S. Pat. Nos. 3,220,972, 3,284,406 and 3,436,366).

In the process for the preparation of the polymers ($A_1$), the various alkaline catalysts can be used, the use of which is recommended for the polymerization of diorganopolysiloxane oligomers (namely, the diorganopolysiloxanes of low molecular weight and low degree of polymerization).

These alkaline catalysts are described, for example, on page 227 of the Noll text indicated above. These alkaline catalysts include the hydroxides of the alkali metals, in particular lithium hydroxide, potassium hydroxide, sodium hydroxide and cesium hydroxide. They also include the silanolates of alkali metals, in particular of potassium or sodium, the alkoxides and the siliconates of alkali metals.

In order to accelerate the reaction, it is advantageous to use, in combination with the alkaline catalyst, a sequestering agent for the cation of the catalyst, in an amount of 0.005 to 2 mol of sequestering agent per hydroxide equivalent of the alkali metal or alkaline earth metal.

Preferred such sequestering agents include the crown ethers described in U.S. Pat. Nos. 4,157,337 and 4,138,543, hereby incorporated by reference, and the tris-(oxoalkyl)-amines described in U.S. Pat. No. 4,362,855 and EP-A-180,527.

Among these sequestering agents, polyheteromacropolycyclic cryptand compounds having two tertiary nitrogen atoms mutually linked via three divalent organic hydrocarbon radicals, and including heteroatoms selected from among oxygen and sulfur, are particularly preferred. These cryptands are described in detail in the U.S. Pat. Nos. 4,138,543 and 4,362,855 noted above.

The preferred cryptands are of the formula:

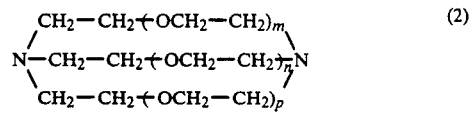

in which m is equal to 2 or 3 and n and p are each 1, 2 or 3.

The compound of the formula (2) in which m=n=p=2 is designated the (2,2,2) cryptand.

The system for catalyzing the polymerization according to the invention can be used in widely varying proportions. It is a particularly surprising and unexpected that it can be used in a very minor amount. Typically, 0.1 to 1,000 mg and preferably 1 to 100 mg of alkali metal hydroxide or alkaline earth metal hydroxide per kg of diorganopolysiloxane charged are used. The hydroxide equivalent for any alkali metal derivative or alkaline earth metal derivative is expressed by the weight of the amount of metal hydroxide which would have to be added and would correspond to the same number of gram atoms of alkali metal or alkaline earth metal as that of the alkali metal derivative or alkaline earth metal derivative used. Moreover, the molar ratio of sequestering agent and hydroxide equivalent of alkali metal or alkaline earth metal typically ranges from 0.005 to 2, and preferably from 0.01 to 1.

The temperature of the polymerization can be within the usual temperature range of from 25° C. to 200° C. and preferably from 80° C. to 180° C. During the polymerization, the water can be removed from the reaction medium (in the case where the starting charge is constituted by the oligomer of the formula (3) with $R_2$=hydroxyl), at the rate of its formation by any appropriate means (azeotropic distillation; removal of water under reduced pressure, and under pressure of an inert gas, in particular nitrogen, etc.). Under these conditions, the catalytic system according to the invention allows the duration of the polymerization reaction to be reduced by a very substantial proportion. This decrease can attain and exceed 75%, relative to the use of the alkaline catalyst alone. When the desired viscosity has been reached, it is recommended to deactivate the catalytic system by addition of a very small amount of an acidic compound, preferably $CO_2$.

From the instant when the polymerization is commenced (time $t_1$) and before terminating this polymerization at the desired degree (time $t_2$), the cyclic or linear polydiorganosiloxane oligomer bearing at least one epoxy-functional radical per molecule is added to the medium of polymerization between $t_1$ and $t_2$.

The times $t_1$ and $t_2$ are estimated conventionally by measuring the viscosity of the reaction mixture.

Also surprisingly and unexpectedly, the epoxy-functional groups are not affected by the basic catalysts, inasmuch as the oligomers are added in the time interval between $t_1$ and $t_2$.

These epoxy-functional groups are not degraded in spite of the alkalinity of the reaction mixture.

Moreover, the epoxy-functional groups are not even degraded when the reaction medium is heated to a temperature of up to 200° C. It is nevertheless desirable to conduct the operation at a temperature below 180° C. and above 80° C.

Such a result can also be obtained if the oligomers bearing at least one epoxy-functional radical are added to the oligomers bearing at least one vinyl group before the start (initiation) of the polymerization. Otherwise, a degradation of the epoxy-functional groups results.

The same applies if an acidic catalyst is used for effecting the polymerization. The oligomers bearing at least one organic epoxy-functional radical are preferably selected from among those of the formulae (3) and (4):

$$R_2-\underset{R}{\underset{|}{Si}}-O-\left[\underset{R}{\underset{|}{Si}}-O\right]_e\left[\underset{A}{\underset{|}{Si}}-O\right]_f\underset{R}{\underset{|}{Si}}-R_2 \quad (3)$$

in which the radicals R and A are as defined for the formula (1) above and $R_2$ is selected from among a radical R, a hydroxyl group and a group A; e is an integer ranging from 0 to 50; and f is an integer ranging from 0 to 20, with the proviso that, if $f=0$, at least one of the radicals $R_2$ is A;

$$\left[\left[\underset{R}{\underset{|}{Si}}-O\right]_g\left[\underset{A}{\underset{|}{Si}}-O\right]_h\right] \quad (4)$$

in which the radicals R and A are as defined for the formula (1) above; g is an integer ranging from 0 to 10, inclusive; and h is an integer ranging from 1 to 10, inclusive, with the proviso that the sum of $g+h$ is at least equal to 3.

The oligomers containing an epoxy-functional group are products which are known to the art and described in the literature; they are described, in particular, in U.S. Pat. Nos. 3,445,877 and 4,252,933, and in FR-A-2,012,012, which are incorporated herein by reference.

They can be prepared without difficulty by a hydrosilylation reaction of the polyhydrogenoorganosiloxanes corresponding to the formulae (3) and (4) in which the radical A has been replaced by a hydrogen atom, on the epoxy-functional organic compound with alkene unsaturation, corresponding to the radical A.

The starting oligomers having a vinyl or epoxy functional group necessary to produce the desired polymers of the formula (1) are easily determined by one skilled in this art.

In the case where it is desired to prepare polymers of the formula (1) in which $R_1$ is a radical R, it suffices for this purpose to add, after the polymerization, for example an organosiliciated compound capable of reacting with the terminal hydroxyl group, for example a silane or a silazane of the formula:

$(R)_3SiCl$, $(R)_3SiNHSi(R)_3$, or to add a blocking agent of the formula:

$(R)_3SiOSi(R)_3$ at the end of the polymerization.

In the same fashion, if it is desired to prepare a polymer of the formula (1) in which $R_1$ is a vinyl radical or a radical A, it suffices to carry out the same operations as above with a silane or a silazane of the formula:

$R_1(R)_2SiCl$, $R_1(R)_2SiNHSi(R)_2R_1$ or a disiloxane of the formula:

$R_1(R)_2Si-O-Si(R)_2R_1$ with $R_1$ representing a vinyl radical or the radical A, respectively.

The polymerization reaction is preferably carried out in bulk, but it is nevertheless possible to use a solvent such as the aliphatic or aromatic hydrocarbons.

The organohydrogenopolysiloxane ($B_1$) which can be used is well known to this art and is described, in particular, in the aforementioned U.S. Pat. Nos. 2,915,497, 3,284,406, 3,436,366 and 3,699,073.

The organohydrogenosiloxane ($B_1$) can be a linear, cyclic or branched polymer, or mixture thereof, comprising siloxane recurring units of the formulae: $RSiO_{1.5}$, $R_2SiO$, $R_3SiO_{0.5}$, $R_2HSiO_{0.5}$, $SiO_2$, $RHSiO$ and $HSiO_{1.5}$.

The catalyst (C) for the polyaddition reaction is a metal or a platinum-based compound (salt or complex).

The platinum catalysts are amply described in the literature, and the complexes of platinum and an organic compound, described in U.S. Pat. Nos. 3,159,601, 3,159,602 and 3,220,972 and European patents EP-A-57,459, EP-A-188,978 and EP-A-190,530, as well as the complexes of platinum and a vinylated organopolysiloxane, described in U.S. Pat. Nos. 3,419,593, 3,715,334, 3,377,432 and 3,814,730, are particularly exemplary.

The platinum catalyst (C) is typically introduced in such an amount that it provides 1 to 500 ppm (parts per million), preferably 5 to 80 ppm of platinum, expressed as metal relative to the total weight of the organopolysiloxanes (A).

The emulsions according to the invention are of the oil-in-water type, and more particularly of the silicone-in-water type (silicone/water emulsion). The emulsions contain an effective amount of at least one surfactant (D) selected from among the anionic, cationic, amphoteric and nonionic surfactants. Such surfactants are described, for example, in U.S. Pat. Nos. 2,891,920, 3,294,725, 3,360,491, 3,983,148 and FR-A-2,605,634, which are incorporated herein by reference.

The preferred anionic surfactants are the alkali metal alkylbenzenesulfonates, alkali metal alkyl-sulfates (or ethoxylated alkylaryl-sulfates) and alkali metal dioctyl-sulfosuccinates.

The preferred cationic surfactants are the quaternary ammonium chlorides and polyethoxylated quaternary ammonium salts.

The preferred nonionic surfactants are the polyethoxylated fatty acids, sorbitan esters, polyethoxylated sorbitan esters, polyethoxylated alkylphenols and polyvinyl alcohols.

In general, 1 to 30 parts by weight, preferably 2 to 10 parts, of surfactant (D) are used per 100 parts by weight of the total amount of the organopolysiloxane polymers (A) and (B).

A more particularly preferred surfactant is polyvinyl alcohol. This is a solid granular product which can still contain pendant acetate groups. Generally, its percentage of hydrolysis is high, exceeding 85%. For example, RHODOVIOL® 25/140 from RHONE-POULENC or ELVANOL® 50–42 from DUPONT can be used. Typically, 1 to 20 parts by weight, preferably 2 to 10 parts, of polyvinyl alcohol are used per 100 parts by weight of the total amount of the organopolysiloxane polymers (A) and (B).

The silicas (E) include the pyrogenic silicas and precipitated silicas.

They have a specific surface area, measured according to the BET method, of at least 50 m$^2$/g, preferably more than 70 m$^2$/g, a mean size of the primary particles of less than 80 nanometers and a bulk density of less than 200 g/liter.

These silicas can be incorporated as such or after having been treated with organosilicon compounds conventionally used for this application. These compounds include methylpolysiloxanes, such as hexamethyldisiloxane and octamethylcyclotetrasiloxane, methylpolysilazanes, such as hexamethyldisilazane, and hexamethylcyclctrisilazane, chlorosilanes, such as dimethyldichlorosilane, trimethylchlorosilane, methylvinyldichlorosilane and dimethylvinylchlorosilane, and alkoxysilanes, such as dimethyldimethoxysilane, dimethylvinylethoxysilane and trimethylmethoxysilane. During this treatment, the silicas can increase their initial weight by up to an amount of 20%, preferably approximately 18%.

The particles prepared by the process of the invention can be used for embedding, encapsulating or dispersing any active principles or active agents, such as, in particular, adhesives, catalysts, colorants, hardeners, detergents, pharmaceutical products, enzymes, perfumes, nutrients, fuels, inks, insecticides, metals, medicaments, monomers, odorizing agents, oils, pheromones, plasticizers, propellants, solvents, solid substrates containing an absorbed active constituent, and vitamins in an elastomer matrix.

The emulsions according to the invention can be prepared by conventional methods of emulsifying organopolysiloxane polymers.

For example, the surfactant (D) and the silica powder (E) can be mixed with water at a temperature ranging from ambient temperature to 80° C. until a homogeneous mixture is obtained. The organopolysiloxanes (A) and (B) are then added to the mixture under continuous vigorous agitation, always at a temperature ranging from 25° to 80° C., in order to form an emulsion. The organopolysiloxanes (A) and (B) can have been dissolved beforehand in an organic solvent.

The particles produced by the process of the invention, which may or may not contain an active principle (G), are more particularly useful as a filler material in matrices of natural or synthetic polymers, in particular in natural or synthetic rubbers and silicone elastomers.

The platinum catalyst (C) and the active principle (G) are then added.

If the active principle (G) is soluble in water and insoluble in the volatile organic solvent, it can be introduced into the original water for the emulsion, preferably up to saturation.

If the active principle (G) is soluble in the volatile organic solvent and insoluble in water, it can be introduced into the solution of the polyorganosiloxanes (A) and (B) in the volatile organic solvent.

If the active principal (G) is insoluble in water and in the volatile organic solvent, it can be introduced in the form of microparticles and dispersed in the organopolysiloxane composition before the latter is emulsified, preferably only in the starting material oil (A). This latter mode of introducing (G) can, of course, be used whatever the solubility of (G) in water and in the volatile organic solvent.

The emulsion is then heated to a temperature (below 100° C.) and for a period of time suitable for the formation of solid particles.

The solution is then cooled to ambient temperature, and the particles are isolated by centrifuging or by filtration through a polyester fabric and washed several times with water in order to eliminate the surfactant and the silica.

After washing with an alcohol, if necessary, preferably methanol, it can be advantageous to mix the particles obtained with silica powder in order to perfect their non-stick property, and then to screen the particles to eliminate the excess silica powder.

Quite surprisingly and unexpectedly, the present invention made it possible to establish that the silica grains are concentrated at the surface of the particles, thus conferring on the latter their non-stick character. The particles are in the form of a powder, the various grains of which do not agglomerate with one another.

In order to further illustrate the present invention and the advantages thereof, the following specific examples are given, it being understood that same are intended only as illustrative and in nowise limitative.

In said examples to follow, as well as in the above description, all parts and percentages are given by weight, unless otherwise indicated.

EXAMPLE 1

An aqueous solution containing:
(i) 1,200 g of distilled water;
(ii) 5 g of the surfactant RHODOVIOL® 25/140, marketed by Rhone-Poulenc; and
(iii) 11.2 g of a precipitated silica having a specific BET surface area of 160 m$^2$/g, was prepared.

100 g of an organopolysiloxane composition formulated by mixing:
(iv) 694 parts of a vinylated polydimethylsiloxane oil blocked at both polymer ends by a vinyldimethylsiloxy group and having a viscosity of 3,500 mPa.s at 25° C.;
(v) 261 parts of dry excipients of a vinyl resin containing 53.5 mol % of $SiO_2$ units, 6 mol % of $(CH_3)(CH_2=CH)SiO$ units and 40 mol % of $(CH_3)_3SiO_{0.5}$ units;

(vi) 45 parts of a hydrogenated liquid silicone resin prepared by hydrolysis of technical silicate $Si(OC_2H_5)_4$ and $(CH_3)_2HSiCl$ in amounts corresponding to 1 mol of $SiO_2$ per 2 moles of $(CH_3)_2HSiCl$ in toluene solution (this resin thus has a theoretical molar ratio of units $(CH_3)HSiO_{0.5}/SiO_2=2$ and a real molar ratio of 2.23); and (vii) 0.02 parts (calculated as platinum metal) of a catalyst solution prepared by mixing 0.6 part of chloroplatinic acid, 10 parts of isopropanol, 55 parts of xylene and 6 parts of 1,1,3,3-tetramethyl-1,3-divinyl-disiloxane at ambient temperature;
were run into the above aqueous solution under vigorous agitation in order to form an emulsion.

The temperature of the water was increased to 50° C., maintained thereat for 15 minutes and then progressively increased to 80° C., and the mixture was maintained under agitation for 1 hour and 30 minutes. The solutions were then cooled to 25° C., and the particles were filtered off over polyester fabric and washed several times with water in order to eliminate the surfactant and the silica.

These particles were recovered and mixed with 4 parts of the same precipitated silica used at the outset, and then placed in a vacuum for 3 hours at 125° C. They were then recovered, screened in order to eliminate the excess silica and fractionated according to particle size.

The mass yield obtained was 90%.

The following distribution of particular diameters $\phi$ of the particles was determined by screening:

| | |
|---|---|
| 200 μm < $\phi$ < 500 μm: | 40% by weight |
| 500 μm < $\phi$ < 1,000 μm: | 60% by weight. |

EXAMPLE 2

An aqueous solution containing:
(i) 600 g of distilled water;
(ii) 3 g of the surfactant MONTANOX ® 20 (a polyethoxy-sorbitan monolaurate, marketed by SEPPIC);
(iii) 4.7 g of precipitated silica having a specific BET surface area of 160 m²/g; and
(iv) 343 g of KCl;
was prepared.

42 parts of the organopolysiloxane composition described in Example 1, 18 g of KCl and 15 g of $CHCl_3$ were run into this aqueous solution at 40° C., under vigorous agitation, in order to form an emulsion.

After stirring for 1 hour and 30 minutes, the temperature was increased to 60° C., maintained at this temperature for 30 minutes before increasing it to 80° C., where it was maintained for 2 hours.

The solution was then cooled to 25° C. and filtered for recovery of the particles and the silica. The entire mass was placed under a vacuum at 125° C. for 3 hours. The product was recovered and screened in order to eliminate the excess silica.

The particles obtained had an extractables content of 4.5% relative to the weight of the organopolysiloxane composition, a mean particle size of 700 μm and a KCl filler content of 15% by weight.

EXAMPLE 3

An aqueous solution containing:
(i) 600 parts of distilled water;
(ii) 2.5 parts of RHODOVIOL ® 25/140;
(iii) 45.2 parts of $KIO_3$; and
(iv) 4.7 parts of precipitated silica having a specific BET surface area of 160 m²/g;
was prepared.

42 parts of the organopolysiloxane composition described in Example 1, 18 g of KCl and 15 g of $CHCl_3$ were run into this aqueous solution maintained at 25° C. under vigorous agitation, in order to form an emulsion. The temperature was gradually increased to 50° C. and maintained thereat for 15 minutes, under stirring, and the temperature was then progressively increased to 80° C. and maintained thereat for 1 hours and 30 minutes, under stirring.

The solution was cooled to 25° C. and filtered in order to recover the particles and the silica. The entire mass was placed under vacuum for 12 hours at 60° C. The product was recovered and screened in order to eliminate the excess silica.

The particles obtained had an extractables content of 5.5% relative to the weight of the organopolysiloxane composition.

This size distribution of the particles obtained was as follows:

| | |
|---|---|
| 200 μm < $\phi$ < 500 μm: | 40% by weight |
| 500 μm < $\phi$ < 1,000 μm: | 60% by weight. |

The content of dispersed KCl in the particles was 22% by weight.

EXAMPLE 4

An aqueous solution containing:
(i) 600 ml of distilled water;
(ii) 2.5 g of the surfactant RHODOVIOL ® 25/140 (polyvinyl alcohol, commercially available from Rhone-Poulenc); and
(iii) 5.6 g of precipitated silica TIXOSIL ® 375, commercially available from Rhone-Poulenc;
was prepared.

The following were added to this mixture, separately in this order:
(iv) 50 g of the organopolysiloxane composition described in Example 1, this composition being added to the aqueous solution under vigorous agitation, in order to form an emulsion;
(v) 21.4 g of a mixture of carboxymethylcellulose and VANTOCIL ® 1B having the following composition:

| | |
|---|---|
| (a) carboxymethylcellulose: | 12.4 g; |
| (b) VANTOCIL 1B: | 9.0 g. |

This mixture was in the form of solid particles having a mean particle size of less than 10 μm; and
(vi) 17.3 g of $CHCl_3$.

The mixture obtained was heated to a temperature of 50° C. for 15 minutes. This temperature was progressively increased to 80° C. and maintained thereat for 1 hour and 30 minutes, the mixture being stirred. The mixture was cooled to 25° C.

The beads formed were filtered off through a polyester fabric and then washed several times with water in order to eliminate the surfactant and the silica.

These beads were recovered and mixed with 2 g of silica TIXOSIL T375 and then placed under a vacuum for 3 hours at 125° C. They were then recovered and screened in order to eliminate the excess silica and to fractionate them according to size.

The mass yield obtained was 93% and the size distribution of the beads was as follows:

| | | | |
|---|---|---|---|
| | φ > | 1 mm: | 25.1% |
| 500 μm < | φ < | 1 mm: | 29.3% |
| 200 μm < | φ < | 500 μm: | 26.8% |
| 100 μm < | φ < | 200 μm: | 14.1% |
| | φ < | 100 μm: | 25.1%. |

The microbeads obtained had an extractables content of 5% relative to the mass of the organopolysiloxane composition introduced.

EXAMPLE 5

The procedure followed was exactly as in Example 4, except that 2.5 g of a supplementary surfactant of anionic type, namely, sodium dodecylsulfate (sodium laurylsulfate), were added to the aqueous solution.

The mass yield was about 70%, giving the following size distribution of the silicone beads obtained:

| | | | |
|---|---|---|---|
| | φ > | 1 mm: | 0% |
| 500 μm < | φ < | 1 mm: | 7.6% |
| 200 μm < | φ < | 500 μm: | 53.3% |
| 100 μm < | φ < | 200 μm: | 28.2% |
| | φ < | 100 μm: | 10.9%. |

The addition of an anionic sodium laurylsulfate surfactant thus enabled microbeads having a better monodispersity of the particle size essentially between 100 and 500 μm to be obtained.

The microbeads obtained had an extractables content of 4.3% relative to the mass of the organopolysiloxane composition introduced.

EXAMPLE 6

An aqueous solution containing:
(i) 600 ml of distilled water;
(ii) 2.5 g of surfactant RHODOVIOL ® 25/140; and
(iii) 5.6 g of precipitated silica TIXOSIL ® 375; was prepared.

The following materials were added to this mixture, separately, in this order:
(iv) 42 g of the organopolysiloxane composition described in Example 1, this composition being added to the aqueous solution under vigorous agitation in order to form an emulsion; and
(v) 5 g of powdered NIVERGOLINE ® base, namely, 1,6-dimethyl-8β-(5-bromonicotinoyloxymethyl)-10α-methoxyergoline, commercially available from Rhone-Poulenc (Laboratoire SPECIA), dissolved in 7.3 g of chloroform.

The procedure then followed was exactly that of Example 4, except that the silicone beads obtained were additionally dried in vacuo for 10 hours at 60° C. The extractables content relative to the mass of the starting organopolysiloxane composition was 7.2%.

The particle size distribution of the beads was as follows:

| | | | |
|---|---|---|---|
| | φ > | 1 mm: | 23.9% |
| 500 μm < | φ < | 1 mm: | 30.5% |
| 200 μm < | φ < | 500 μm: | 24.6% |
| 100 μm < | φ < | 200 μm: | 15.2% |
| | φ < | 100 μm: | 5.8%. |

EXAMPLE 7

An aqueous solution containing:
(i) 900 ml of distilled water;
(ii) 3.6 g of surfactant RHODOVIOL ® 25/140 commercially available from Rhone-Poulenc; and
(iii) 12 g of precipitated silica having a specific BET surface area of 160 m²/g; was prepared.

100 g of an organopolysiloxane composition obtained by mixing:
(iv) 14.5 g of a polyorganohydrogenosiloxane bearing an epoxy-functional group, having the average formula:

$$(CH_3)_3Si-O+Si(CH_3)(CH_3)-O\overline{)_{8.3}}(Si(CH_3)(H)-O\overline{)_{8}}(Si(CH_3)((CH_2)_3-O-CH_2-CH(-O-)CH_2)-O\overline{)_{19}}Si(CH_3)_3$$

(v) 85.5 g of a polydimethylsiloxane blocked at each end of its polymer chain by a dimethylvinylsiloxy unit and having a viscosity of 600 mPa.s at 25° C.; and
(vi) 15 mg of a platinum solution in hexane, providing 8.7% of platinum metal by titration, were run into this aqueous solution under vigorous agitation in order to form an emulsion.

The temperature of the water was increased to 50° C., maintained thereat for 15 minutes and then progressively increased to 80° C. and maintained thereat for 1 hour and 30 minutes, under stirring. These solutions were then cooled to 25° C., and the microbeads were filtered off over polyester fabrics and washed several times with distilled water, in order to eliminate the surfactant and the silica.

These beads were recovered and mixed with four parts of the same pyrogenic silica used at the beginning of the experiment and then placed under a vacuum for 3 hours at 125° C. They were then recovered, screened to eliminate the excess silica and fractionated according to particle size.

The mass yield obtained was 90%.

The microbeads obtained had an extractables content of 2.1% relative to the weight of the composition.

By passage through a screen, the following distribution of the particle diameter (φ) of the microbeads was determined:

| | | | |
|---|---|---|---|
| 100 μm < | φ < | 200 μm: | 19.2% |
| 200 μm < | φ < | 500 μm: | 52.1% |
| 500 μm < | φ < | 1,000 μm: | 28.7%. |

EXAMPLE 8

An aqueous solution containing:
(i) 900 ml of distilled water;
(ii) 3.62 g of surfactant RHODOVIOL ® 25/140 commercially available from Rhone-Poulenc; and
(iii) 12 g of precipitated silica having a specific BET surface area of 160 m²/g; was prepared.

100 g of an organopolysiloxane composition formulated by mixing:

(iv) 10 g of a polyorganohydrogenosiloxane bearing an epoxy-functional group and having the average formula:

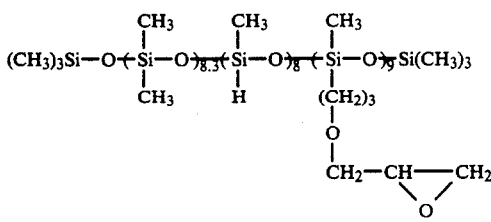

(v) 90 g of a polydimethylsiloxane bearing an epoxy-functional group and having the average formula:

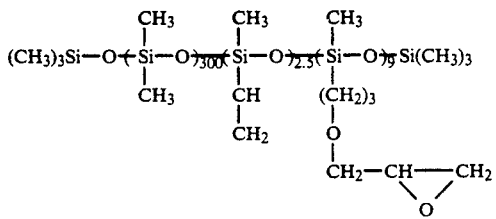

(vi) 30 mg of a solution of platinum in hexane, providing 8.7% of platinum metal by titration;
was run into this aqueous solution, under vigorous agitation, in order to form an emulsion.

The temperature of the water was increased to 50° C., maintained thereat for 15 minutes and then progressively increased to 80° C. and maintained thereat from 1 hour and 30 minutes, under stirring. The solutions were then cooled to 25° C., and the microbeads were filtered off over polyester fabrics and washed several times with distilled water in order to remove the surfactant and the silica.

These beads were recovered and mixed with 4 parts of the same pyrogenic silica used at the beginning of the experiment, and then placed under a vacuum for 3 hours at 125° C. They were then recovered, screened to remove the excess silica and fractionated according to particle size.

The mass yield obtained was 90%.

The microbeads obtained had an extractables content of 5.2% relative to the weight of the composition.

By passing through a screen, the following distribution of the particle diameter ($\phi$) of the microcapsules was determined:

| | |
|---|---|
| 2 μm > $\phi$ > 400 μm: | 58% |
| 100 μm < $\phi$ < 400 μm: | 42%. |

COMPARATIVE EXAMPLES 9, 10 AND 11

The procedure of Examples 1, 2 and 3 was repeated exactly, except that no precipitated silica was introduced.

This resulted in the production of sticking particles, agglomerated with one another and consequently useless, in each of the three comparative experiments.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of non-stick elastomeric organopolysiloxane particulates having a mean particle size ranging from 50 μm to 3 mm, comprising
   (a) forming an oil-in-water emulsion comprising:
   (A) 100 parts by weight of a polydiorganosiloxane bearing at least two Si-vinyl groups per molecule;
   (B) an organohydrogenopolysiloxane having at least three SiH groups per molecule in such amount that the SiH/SiVi molar ratio ranges from 0.6 to 8;
   (C) a catalytically effective amount of a platinum curing catalyst;
   (D) an effective amount of a surfactant of oil-in-water type;
   (E) 3 to 100 parts by weight of a pyrogenic or precipitated silica powder; and
   (F) water, and
   (b) polyaddition crosslinking said emulsion into desired particles by heating same to a temperature ranging from 40° to 100° C.

2. The process as defined by claim 1, said SiH/SiVi molar ratio ranging from 0.8 to 4 and comprising from 5 to 30 parts by weight of said pyrogenic or precipitated silica powder (E).

3. The process as defined by claim 1, said polydiorganosiloxane (A) comprising at least one organic epoxy-functional group having from 4 to 20 carbon atoms.

4. The process as defined by claim 1, said organohydrogenopolysiloxane (B) comprising at least one organic epoxy-functional group having from 4 to 20 carbon atoms.

5. The process as defined by claim 1, further comprising a volatile organic solvent having a boiling point of less than 100° C.

6. The process as defined by claim 5, said volatile organic solvent comprising chloroform.

7. The process as defined by claim 1, further comprising (G) at least one active principle.

8. The process as defined by claim 1, said polydiorganosiloxane (A) comprising a vinylated oil having a viscosity ranging from 100 to 300,000 mPa.s at 25° C.

9. The process as defined by claim 1, said polydiorganosiloxane (A) comprising an MQ resin.

10. The process as defined by claim 1, comprising from 1 to 500 ppm of platinum.

11. The process as defined by claim 1, said surfactant comprising a polyvinyl alcohol.

12. The process as defined by claim 1, said silica powder (E) having a specific surface area of at least 50 m²/g, a mean primary particle size of less than 80 nanometers and a bulk density of less than 200 g/liter.

13. The process as defined by claim 7, said active principle (G) comprising an adhesive, catalyst, colorant, hardener, detergent, pharmaceutical, enzyme, perfume, nutrient, fuel, ink, insecticide, metal, medicament, monomer, odorizing agent, oil, pheromone, plasticizer, propellant, solvent, solid substrate which comprises an absorbed active agent, or a vitamin dispersed in an elastomeric matrix.

14. The process as defined by claim 7, comprising microfine particles of said active principle (G).

15. The non-stick elastomeric organopolysiloxane particulates prepared by the process as defined by claim 1.

16. In a filled matrix of a natural or synthetic polymer, the improvement which comprises, as the filler material therefor, the non-stick elastomeric organopolysiloxane particulates as defined by claim 15.

17. The non-stick elastomeric organopolysiloxane particulates as defined by claim 15, having a mean particle size ranging from 100 μm to 1 mm.

18. The non-stick elastomeric organopolysiloxane particulates as defined by claim 15, having a uniform coating of silica powder concentrated at the surface thereof.

19. A process for the preparation of non-stick elastomeric organopolysiloxane particulates having a mean particle size ranging from 50 μm to 3 mm according to the process of claim 1, wherein said heating step includes at least one progressive temperature increase within the range of between about 40° C. and 100° C. wherein the pre-incremented and post-incremented temperatures are maintained essentially constant for a period of time sufficient to facilitate the formation of the non-stick elastomeric organopolysiloxane particulates.

20. A process for the preparation of non-stick elastomeric organopolysiloxane particulates having a mean particle size ranging from 50 μm to 3 mm according to the process of claim 19, wherein said period of time during which said pre-incremented and post-incremented temperatures are maintained essentially constant is at least 15 minutes.

21. The process as defined by claim 1, further comprising (H) at least one volatile organic solvent.

* * * * *